(12) United States Patent
Kiyotoh et al.

(10) Patent No.: US 10,071,155 B2
(45) Date of Patent: Sep. 11, 2018

(54) NASAL MUCOSAL VACCINE COMPOSITION

(71) Applicant: NITTO DENKO CORPORATION, Osaka (JP)

(72) Inventors: Eiji Kiyotoh, Osaka (JP); Mitsuhiko Hori, Osaka (JP); Katsuyuki Okubo, Osaka (JP); Daisuke Asari, Osaka (JP); Arimichi Okazaki, Osaka (JP); Masahiro Fukasaka, Osaka (JP); Kyohei Matsushita, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

(21) Appl. No.: 14/916,721

(22) PCT Filed: Oct. 2, 2014

(86) PCT No.: PCT/JP2014/076346
§ 371 (c)(1),
(2) Date: Mar. 4, 2016

(87) PCT Pub. No.: WO2015/050178
PCT Pub. Date: Apr. 9, 2015

(65) Prior Publication Data
US 2016/0228540 A1    Aug. 11, 2016

(30) Foreign Application Priority Data

Oct. 3, 2013    (JP) ................. 2013-208665

(51) Int. Cl.
| | |
|---|---|
| *A61K 39/00* | (2006.01) |
| *A61K 39/39* | (2006.01) |
| *A61K 39/08* | (2006.01) |
| *A61K 39/09* | (2006.01) |
| *A61K 39/12* | (2006.01) |
| *A61K 39/125* | (2006.01) |
| *A61K 39/13* | (2006.01) |
| *A61K 39/145* | (2006.01) |
| *A61K 39/15* | (2006.01) |

(Continued)

(52) U.S. Cl.
CPC .............. *A61K 39/39* (2013.01); *A61K 39/00* (2013.01); *A61K 39/0011* (2013.01); *A61K 39/08* (2013.01); *A61K 39/092* (2013.01); *A61K 39/12* (2013.01); *A61K 39/125* (2013.01); *A61K 39/13* (2013.01); *A61K 39/145* (2013.01); *A61K 39/15* (2013.01); *A61K 39/165* (2013.01); *A61K 39/205* (2013.01); *A61K 39/25* (2013.01); *A61K 2039/5252* (2013.01); *A61K 2039/5254* (2013.01); *A61K 2039/543* (2013.01); *A61K 2039/55572* (2013.01); *A61K 2039/575* (2013.01); *C12N 2710/16734* (2013.01); *C12N 2710/20034* (2013.01); *C12N 2720/12334* (2013.01); *C12N 2760/18434* (2013.01); *C12N 2760/18734* (2013.01); *C12N 2760/20134* (2013.01); *C12N 2770/24134* (2013.01); *C12N 2770/32434* (2013.01); *C12N 2770/32634* (2013.01); *C12N 2770/36234* (2013.01)

(58) Field of Classification Search
None
See application file for complete search history.

(56) References Cited

U.S. PATENT DOCUMENTS

2005/0152919 A1* 7/2005 Ward .................. A61K 39/165
424/212.1
2008/0279926 A1   11/2008 Vandepapeliere
(Continued)

FOREIGN PATENT DOCUMENTS

| JP | H08-245702 A | 9/1996 |
|---|---|---|
| JP | 2007-505836 A | 3/2007 |

(Continued)

OTHER PUBLICATIONS

He et al., "Modulation of Mucosal Immune Response by Bacterial Lipopolysaccharide in Nasal Vaccination Models", Journal of Dental Health, 2012, vol. 62, No. 2, pp. 263.

International Search Report issued with respect to application No. PCT/JP2014/076346, dated Dec. 16, 2014.

International Preliminary Report on Patentability issued with respect to application No. PCT/JP2014/076346, dated Apr. 5, 2016.

Sapta et al., "Mucosal Adjuvanticity of bacterial lipopolysaccharide in compared with cholera toxin", Proceedings of the Japanese Society for Immunology, 2012, vol. 41., pp. 89.

Extended European Search Report for counterpart EP Application. No. 14850738.7 dated Jun. 8, 2017.

(Continued)

*Primary Examiner* — Brian Gangle
(74) *Attorney, Agent, or Firm* — Greenblum & Bernstein, P.L.C.

(57) ABSTRACT

The present invention provides a nasal mucosal vaccine composition which is safe, useful as a preventive or therapeutic agent for infectious diseases or cancers, and capable of inducing systemic immune responses and mucosal immune responses effectively. The present invention provides a nasal mucosal vaccine composition to be administered to a human or animal nasal mucous membrane, the nasal mucosal vaccine composition containing at least one antigen excluding antigens derived from influenza viruses; and as an adjuvant, a lipopolysaccharide derived from at least one gram-negative bacterium selected from the group consisting of *Serratia, Leclercia, Rahnella, Acidicaldus, Acidiphilium, Acidisphaera, Acidocella, Acidomonas, Asaia, Belnapia, Craurococcus, Gluconacetobacter, Gluconobacter, Kozakia, Leahibacter, Muricoccus, Neoasaia, Oleomonas, Paracraurococcus, Rhodopila, Roseococcus, Rubritepida, Saccharibacter, Stella, Swaminathania, Teichococcus, Zavarzinia, Pseudomonas, Achromobacter, Bacillus, Methanoculleus, Methanosarcina, Clostridium, Micrococcus, Flavobacterium, Pantoea, Acetobacter, Zymomonas, Xanthomonas*, and *Enterobacter*, or a salt thereof.

6 Claims, 2 Drawing Sheets

(51) Int. Cl.
*A61K 39/165* (2006.01)
*A61K 39/205* (2006.01)
*A61K 39/25* (2006.01)

(56) References Cited

U.S. PATENT DOCUMENTS

| | | | |
|---|---|---|---|
| 2010/0312045 | A1 | 12/2010 | Ramlov et al. |
| 2013/0266612 | A1* | 10/2013 | Fukasaka ............... A61K 39/39 424/210.1 |
| 2014/0193460 | A1 | 7/2014 | Spector et al. |
| 2014/0220058 | A1* | 8/2014 | Maeda ................. A61K 9/0014 424/185.1 |

FOREIGN PATENT DOCUMENTS

| | | |
|---|---|---|
| JP | 4043533 B2 | 2/2008 |
| JP | 2009-242367 A | 10/2009 |
| JP | 2012-82156 A | 4/2012 |
| JP | 5650780 B2 | 1/2015 |
| WO | 96/23002 A1 | 8/1996 |
| WO | 2005/027964 A1 | 3/2005 |
| WO | 2007/068907 A2 | 6/2007 |
| WO | 2009/065415 A1 | 5/2009 |
| WO | 2013/006569 A2 | 1/2013 |

OTHER PUBLICATIONS

Arenas, "The Role of Bacterial Lipopolysaccharides as Immune Modulator in Vaccine and Drug Development", Endocrine, Metabolic & Immune Disorders—Drug Targets 2012, 12(3):221-235.
Hiebijima et al., Abstract EP-6: "Effect of immune-potentiator from Pantoea aggromelans 1 (IP-PA1) on reduction of Salmonella vaccine reactivity in steroid-administered stress model fown", Abstracts of Annual Meeting of the Japanese Society of Veterinary Science 2009, 147:256.
Office Action issued in JP 2014-204025, dated Jun. 12, 2018.
Russian Office Action issued with respect to Application No. 2016109366, dated Jun. 14, 2018.

* cited by examiner

NASAL MUCOSAL VACCINE COMPOSITION

TECHNICAL FIELD

The present invention relates to a nasal mucosal vaccine composition useful as a preventive or therapeutic agent for infectious diseases or cancers. The present invention specifically relates to a nasal mucosal vaccine composition which contains a specific lipopolysaccharide as an adjuvant and is capable of inducing systemic immune responses and mucosal immune responses safely and effectively when it is administered to a nasal mucosa together with an antigen.

BACKGROUND ART

Most of the commercially available vaccine preparations are in the form of injections. Injectable vaccines induce immune responses in the blood, i.e. systemic immune responses (production of IgG antibodies), but induce no mucosal immune responses (production of IgA antibodies). Although they can prevent the proliferation of pathogens after infection, such vaccines have difficulty in preventing the infection itself of pathogens via the mucosal routes.

This difficulty currently arouses an attention to mucosal vaccination, and vaccine researchers especially direct their attention to the development of vaccines for mucosal administration (nasal administration) using influenza viruses as antigens.

Vaccines for mucosal administration can induce not only systemic immunity (production of IgG antibodies) but also mucosal immunity (production of IgA antibodies). The IgA antibodies characteristically do not strictly distinguish the types of pathogens of the target disease. Thus, the IgA antibodies can respond to possible annual changes in types of circulating pathogens, and are considered to be effective in preventing pandemics.

One reason for such attention to vaccines for nasal administration is as follows. That is, administration of an antigen to a digestive tract mucosa is easily affected by gastric acid and proteases and is difficult to avoid such affection; in contrast, administration of an antigen via a nasal mucosa is not affected by such factors. Another reason is that the nasal mucosa has an antigen-recognizing tissue, called NALT, thereon and this tissue is effective for immune responses.

The following documents report examples of vaccines for nasal administration.

Patent Literature 1 proposes a *Pantoea*-derived lipopolysaccharide (LPS) and discloses that this LPS is safer and more enhances an immune response than conventional LPSs when administered together with an antigen.

However, Patent Literature 1 fails to mention or exemplify clearly the use of acquired immunity and to show an optimal ratio between the adjuvant and the antigen. Patent Literature 1 further fails to mention clearly the use of a *Pantoea*-derived LPS as a mucosal vaccine.

Patent Literature 2 proposes an inactivated antigen of a pathogen and, as an immunostimulant (adjuvant), a vaccine including a combination of Poly (I:C) and zymosan. The literature discloses one example using a lipopolysaccharide (LPS) derived from *Pantoea agglomerans* as an adjuvant and an influenza virus as a pathogen.

Still, the vaccine disclosed in Patent Literature 2 is unclear whether or not it can affect antigens other than the influenza viruses when nasally administered.

CITATION LIST

Patent Literature

Patent Literature 1: JP 4043533 B
Patent Literature 2: JP 2009-242367 A

SUMMARY OF INVENTION

Technical Problem

In consideration of the above situation, the present invention aims to provide a nasal mucosal vaccine composition which is safe, useful as a preventive or therapeutic agent for infectious diseases or cancers, and capable of inducing systemic immune responses and mucosal immune responses effectively.

Solution to Problem

The present inventors have performed studies for achieving the above aim, and have thereby found that nasal mucosal administration of a lipopolysaccharide derived from a specific gram-negative bacterium or a salt thereof as an adjuvant together with an antigen excluding the influenza antigens leads to safe and effective induction of systemic immune responses and mucosal immune responses. The present inventors have finally completed the present invention.

That is, the present invention is a nasal mucosal vaccine composition to be administered to a human or animal nasal mucous membrane, the nasal mucosal vaccine composition containing at least one antigen excluding antigens derived from influenza viruses, and, as an adjuvant, a lipopolysaccharide derived from at least one gram-negative bacterium selected from the group consisting of *Serratia, Leclercia, Rahnella, Acidicaldus, Acidiphilium, Acidisphaera, Acidocella, Acidomonas, Asaia, Belnapia, Craurococcus, Gluconacetobacter, Gluconobacter, Kozakia, Leahibacter, Muricoccus, Neoasaia, Oleomonas, Paracraurococcus, Rhodopila, Roseococcus, Rubritepida, Saccharibacter, Stella, Swaminathania, Teichococcus, Zavarzinia, Pseudomonas, Achromobacter, Bacillus, Methanoculleus, Methanosarcina, Clostridium, Micrococcus, Flavobacterium, Pantoea, Acetobacter, Zymomonas, Xanthomonas,* and *Enterobacter*, or a salt thereof.

In the nasal mucosal vaccine composition of the present invention, a mass ratio between the adjuvant and the antigen (total mass of the adjuvant/total mass of the antigen) is preferably 0.002 to 500.

The nasal mucosal vaccine composition of the present invention is preferably used for inducing the humoral immunity.

In the nasal mucosal vaccine composition of the present invention, the antigen is preferably an antigen derived from an infectious disease or a cancer antigen.

The present invention will be described in detail below.

The nasal mucosal vaccine composition of the present invention contains at least one antigen and an adjuvant.

In the nasal mucosal vaccine composition of the present invention, the ratio of the total mass of the adjuvant to the total mass of the antigen is preferably 0.002 to 500. If this ratio is lower than 0.002, the vaccine composition may fail to induce sufficiently high immunity. If the ratio is higher than 500, the vaccine composition may involve the issue of safety. The ratio by mass of the adjuvant to the antigen is more preferably 0.01 or higher but 100 or lower. The vaccine composition containing the adjuvant and the antigen at a ratio by mass within this range can induce sufficiently high immunity while maintaining the safety.

The term "mass of the antigen" herein means the mass of the antigenic protein contained in an antigen in the vaccine, unless otherwise specified. Thus, for antigens derived from organisms, such as viruses, the mass of the antigen means the sum of the masses of all the proteins contained in the antigen.

The antigen may be selected from infectious-disease antigens (excluding the influenza-derived antigens) and cancer antigens. Influenza viruses are rapidly mutating viruses. Thus, circulating virus strains change year by year and vaccines for such influenza need to be produced from the antigens corresponding to the circulating virus strains. The vaccine compositions thus produced require further attention to their characteristics, such as stability. Since the present invention aims to cover antigens which less often mutate, preferably infectious-pathogen-derived antigens, it excludes the influenza-derived antigens.

The antigen used in the present invention is preferably selected from infectious-pathogen-derived antigens, excluding the influenza-derived antigens, and cancer antigens.

For infectious-disease-derived antigens, prior development of antibodies against the diseases by vaccination is required so as to prevent the diseases caused by these antigens. Thus, the use of the present invention is preferred. The mucosal vaccine composition of the present invention is suitable for activating humoral immunity.

The antigen used in the present invention is preferably selected from infectious-disease-derived antigens excluding the influenza-derived antigens, and the infectious-disease-derived antigens may be any infectious pathogens and antigens derived from the infectious pathogens excluding the influenza-derived antigens.

Examples of diseases caused by the above infectious pathogens excluding the influenza-derived antigens include, but not limited to, viral diseases due to infection caused by viruses, such as adenoviruses, herpesviruses (e.g. HSV-I, HSV-II, CMV, VZV), poxviruses (e.g. orthopoxviruses such as variola virus, vaccinia virus, and molluscum contagiosum virus), picornaviruses (e.g. rhinoviruses and enteroviruses), paramyxoviruses (e.g. parainfluenza viruses, mumps virus, measles virus, respiratory syncytial virus (RSV)), coronaviruses (e.g. SARS), papovaviruses (e.g. human papillomaviruses causing genital warts, verruca vulgaris, plantar warts, or the like), hepadnaviruses (e.g. Hepatitis B virus), flaviviruses (e.g. Hepatitis C virus, Dengue virus), and retroviruses (e.g. lentiviruses such as HIV); bacterial diseases due to infection caused by bacteria, such as the genera *Escherichia, Enterobacter, Salmonella, Staphylococcus, Shigella, Listeria, Aerobacter, Helicobacter, Klebsiella, Proteus, Pseudomonas, Streptococcus, Chlamydia*, and *Mycoplasma, Streptococcus pneumoniae*, the genera *Neisseria, Clostridium, Bacillus, Corynebacterium, Mycobacterium, Campylobacter, Vibrio, Serratia, Providencia, Chromobacterium, Brucella, Yersinia, Haemophilus*, and *Bordetella*; mycoses typified by, but not limited to, *Chlamydia*, candidiasis, aspergillosis, histoplasmosis, and *cryptococcal meningitis*; and other infectious diseases such as malaria, *Pneumocystis carinii* pneumonia, leishmaniasis, cryptosporidiosis, toxoplasmosis, and trypanosomiasis.

The infectious-disease-derived antigen in the present invention is preferably at least one selected from the group consisting of antigens derived from human papillomaviruses and antigens derived from *Streptococcus pneumoniae*.

The nasal mucosal vaccine composition of the present invention at least contains an effective dose of the antigen. For example, the amount of an antigen contained in the nasal mucosal vaccine composition of the present invention is preferably within the range of 0.01 to 10000 μg per dose. Less than 0.01 μg of an antigen may cause insufficient functions as a preventive or therapeutic agent for infectious diseases or cancers. More than 10000 μg thereof may cause safety issues. The antigen content is more preferably 0.1 μg or more, whereas more preferably 5000 μg or less.

The nasal mucosal vaccine composition of the present invention contains an adjuvant.

Examples of the adjuvant include Toll-like receptor 4 (TLR4) agonists. The Toll-like receptor 4 (TLR4) agonist in the present invention is a specific lipopolysaccharide, or a derivative or salt thereof.

The term "lipopolysaccharide" herein means not only the lipopolysaccharide itself but also a derivative thereof as long as it has the characteristics of the lipopolysaccharide. The "salt" herein may be any salts of organic acids and inorganic acids, and it is preferably a pharmaceutically acceptable salt.

The following will describe the lipopolysaccharides (also abbreviated as LPSs).

The LPSs are complex compounds of lipids and saccharides existing on the outer membranes that surround the peptidoglycan of the cell walls of Gram-negative bacterium, such as *Escherichia coli, Salmonella* species, and *Bordetella pertussis*. They are known as active ingredients of O-antigens and endotoxins (J. M. Ghuysen and R. Hakenbeck (Eds.), "Bacterial Cell Wall", New Comprehensive Biochemistry, Vol. 27, p. 18, Elsevier, 1994).

The basic structure of the LPS includes three components: a lipid A unit having a specific lipid; an oligosaccharide unit, called an R-core, which covalently bonds to the Lipid A; and an O-specific polysaccharide unit ("Nikkei Biotechnology Saishin Yougo Jiten", p. 431, Nikkei McGraw-Hill, Inc., 1985).

The O-specific polysaccharide has the most variety of structures among the constitutional units. The structure thereof is specific to the type of a bacterial species, and shows an activity as what is called an O-antigen. A usual O-specific polysaccharide characteristically has a structure constituted by a repeating oligosaccharide unit which contains a small number of monosaccharides. Also known as structures of the O-specific polysaccharide are those constituted by a repeating oligosaccharide which contains a single monosaccharide and those having no repeating unit.

The nasal mucosal vaccine composition of the present invention contains a lipopolysaccharide derived from a specific gram-negative bacterium or a salt thereof as the aforementioned adjuvant.

They are contained in many foods and herbal medicines, and thus the safety thereof in living bodies is ensured.

Examples of bacteria from which a lipopolysaccharide for use in the adjuvant is derived include *Serratia* (species closely related to *Pantoea*/bread, meat, milk, one species of indigenous bacteria), *Leclercia* (species closely related to *Pantoea*/foods in general (soil bacteria)), *Rahnella* (species closely related to *Pantoea*/one species of indigenous bacteria), *Acidicaldus* (acetic bacteria/fermented food production), *Acidiphilium* (acetic bacteria/fermented food production), *Acidisphaera* (acetic bacteria/fermented food production), *Acidocella* (acetic bacteria/fermented food production), *Acidomonas* (acetic bacteria/fermented food production), *Asaia* (acetic bacteria/fermented food production), *Belnapia* (acetic bacteria/fermented food production), *Craurococcus* (acetic bacteria/fermented food production), *Glu-*

*conacetobacter* (acetic bacteria/fermented food production), *Gluconobacter* (acetic bacteria/fermented food production), *Kozakia* (acetic bacteria/fermented food production), *Leahibacter* (acetic bacteria/fermented food production), *Muricoccus* (acetic bacteria/fermented food production), *Neoasaia* (acetic bacteria/fermented food production), *Oleomonas* (acetic bacteria/fermented food production), *Paracraurococcus* (acetic bacteria/fermented food production), *Rhodopila* (acetic bacteria/fermented food production), *Roseococcus* (acetic bacteria/fermented food production), *Rubritepida* (acetic bacteria/fermented food production), *Saccharibacter* (acetic bacteria/fermented food production), *Stella* (acetic bacteria/fermented food production), *Swaminathania* (acetic bacteria/fermented food production), *Teichococcus* (acetic bacteria/fermented food production), *Zavarzinia* (acetic bacteria/fermented food production), *Pseudomonas* (*Pseudomonas* bacteria/beef, egg, meat, fish, vegetable), *Achromobacter* (*Achromobacter* bacteria/fish, meat), *Bacillus* (*Bacillus* bacteria/rice, vegetable), *Methanoculleus* (methane-producing bacteria/methane-producing bacterium parasitizing on animal intestines), *Methanosarcina* (methane-producing bacteria/methane-producing bacterium parasitizing on animal intestines), *Clostridium* (*Clostridium* bacteria/meat, milk, vegetable, canned food), *Micrococcus* (*Actinomycetes*/meat, fish), *Flavobacterium* (*Bacteroides* bacteria/putrefactive bacterium of food), *Pantoea, Acetobacter, Zymomonas, Xanthomonas*, and *Enterobacter*. These are assured to be safe to the living body because these are contained in many foods, or used in the course of producing foods.

Among these, at least one selected from the group consisting of *Serratia, Leclercia, Rahnella, Acidicaldus, Acidiphilium, Acidisphaera, Acidocella, Acidomonas, Asaia, Belnapia, Craurococcus, Gluconacetobacter, Gluconobacter, Kozakia, Leahibacter, Muricoccus, Neoasaia, Oleomonas, Paracraurococcus, Rhodopila, Roseococcus, Rubritepida, Saccharibacter, Stella, Swaminathania, Teichococcus*, and *Zavarzinia* is preferred.

More preferably, the gram-negative bacterium is at least one selected from the group consisting of *Pantoea, Acetobacter, Zymomonas, Xanthomonas*, and *Enterobacter*. In particular, *Pantoea*-derived components are currently used as health food, and are thus considered to be more effective especially in administration to mucosal surfaces. Extracts derived from these bacterial species or modified products thereof can be used as they are.

Lipopolysaccharides derived from the gram-negative bacterium or a salt thereof need to take into account the safety in living bodies, and they may be used as modified products for detoxification thereof.

Examples of the Toll-like receptor 4 (TLR 4) agonist include derivatives of the specific lipopolysaccharides, such as Lipid A obtainable by removing the polysaccharide portion from a lipopolysaccharide or monophosphoryl lipid A, 3-deacylated MPL and the like. They may be in the form of a salt.

The Lipid A obtainable by removing the polysaccharide portion from a lipopolysaccharide is at least an isolated product from the specific gram-negative bacterium. This may be a product synthesized so as to have the same structure as the isolated product from the gram-negative bacterium.

The modified product of the Lipid A may suitably be a dephosphorylated monophosphoryl lipid (MPL) or a salt thereof. The term "monophosphoryl lipid" herein means not only the monophosphoryl lipid itself but also a derivative thereof as long as it has the characteristics thereof. Particularly preferred for the safety in living bodies are 3-deacylated monophosphoryl lipid (3D-MPL), which already produces actual results as an adjuvant in medical applications, and non-deacylated synthesized Glucopyranosyl lipid proposed in US 2010/0310602.

The monophosphoryl lipid may also suitably be Salmonella-derived one which has successfully been administered previously and thus the safety of which has been ensured.

In the present invention, an LPS derived from *Pantoea agglomerans* is preferably used. In particular, the LPS derived from *Pantoea agglomerans* preferably has a molecular weight of 5000±3000, more preferably 5000±2000, which is determined by SDS-PAGE using a protein marker. The molecular weight herein is determined in accordance with the positions of color bands in the SDS-PAGE using a protein marker. This will be described in detail below.

*Pantoea agglomerans*-derived LPSs favorably used in the present invention are lipopolysaccharides whose O-antigen unit characteristically has a structure of repeating rhamnose and glucose units.

The *Pantoea agglomerans*-derived LPS can be produced by culturing *Pantoea agglomerans* by a usual method, collecting the bacterial cells from the medium, and purifying the LPS from the collected bacterial cells by a known method.

The molecular weight of the LPS derived from *Pantoea agglomerans* can be measured by the following method.

Specifically, the following method enables measurement of the molecular weight of a *Pantoea agglomerans*-derived LPS prepared as a compound or a *Pantoea agglomerans*-derived LPS extracted and purified from the vaccine composition by an appropriate method.

An LPS derived from *Pantoea agglomerans* is dissolved in distilled water to prepare a 1 mg/mL solution thereof. The solution prepared and Sample buffer solution 2ME+ (Wako Pure Chemical Industries, Ltd.) are mixed in equal amounts. The mixture is immersed in a boiling water bath for 5 minutes, and immediately thereafter the mixture is immersed in ice water to cool rapidly.

A slab gel electrophoresis unit (Marisol Corp.) is filled with a running buffer (ATTO CORP.). A 20% polyacrylamide gel is fixed on the electrophoresis unit, and 10 μL portions of the sample are loaded into sample wells. Then, the samples are continuously subjected to electrophoresis for at least one hour at a voltage of 100 V until the coloring matter is eluted from the gel. After completion of the electrophoresis, the gel is silver-stained at room temperature using a silver stain kit 161-0443 (Bio-Rad Laboratories, Inc.), examining the behavior of the silver stain.

As long as the nasal mucosal vaccine composition of the present invention contains as the aforementioned adjuvant a specific Gram-negative bacterium-derived lipopolysaccharide or a salt thereof, such an adjuvant may be used in combination with any of other conventionally known adjuvants.

The nasal mucosal vaccine composition of the present invention can be produced by mixing the aforementioned antigen and adjuvant with other components (for example, a phosphate buffer) as appropriate and stirring the mixture by a known method, and further heating, cooling, or no-heat drying the mixture by a known method as appropriate.

The nasal mucosal vaccine composition of the present invention may be used for preparation of liquid medicines, semi-solid medicines, solid medicines, and spray medicines. In the preparation, the aforementioned materials may appropriately be used with any additives such as vehicles, binding agents, perfumes, flavoring agents, sweeteners, colorants, antiseptics, antioxidants, stabilizing agents, and surfactants, if desired.

These materials are not particularly limited and conventionally known ones can be used.

The nasal mucosal vaccine composition of the present invention is preferably a liquid medicine, a spray medicine, a semi-solid medicine, or a solid medicine. As will be mentioned later, the nasal mucosal vaccine composition of the present invention in the form of a liquid medicine, a spray medicine, a semi-solid medicine, or a solid medicine can suitably be administered to the nasal mucosae of humans or animals.

Since the nasal mucosal vaccine composition of the present invention is administered to the nasal mucosae of humans or animals, the semi-solid medicine or the solid medicine thereof is preferably dissolved by body fluids and/or body temperature.

The nasal mucosal vaccine composition of the present invention is administered to the nasal mucosae of humans or animals (e.g. mammals, birds).

The nasal mucosal vaccine composition of the present invention may be administered by a conventionally known method. The dosage thereof is determined in accordance with the animal species, the age, the sex, the body weight, and the like of the subject. For example, when Streptococcus pneumoniae is used as an antigen, 0.1 µg to 50 µg of the composition can usually be administered once or twice or more times. Multiple dose administration is preferred and, in this case, the composition is preferably administered every one to four weeks.

Advantageous Effects of Invention

The nasal mucosal vaccine composition of the present invention contains at least one antigen together with the aforementioned specific adjuvant. Thus, administration of the composition to nasal mucosae can safely and effectively induce humoral immunity, such as systemic immune responses and mucosal immune responses.

DESCRIPTION OF EMBODIMENTS

The present invention will be described in detail below referring to, but not limited to, the following examples.

Examples 1 to 5 and Comparative Examples 1 to 4

The vaccine composition was prepared on the assumption that each administration group consists of 10 mice.

A solution containing a *Streptococcus pneumoniae* capsule polysaccharide (PNEUMOVAX NP, MSD K.K.) (1150 µg/mL) and a solution of a *Pantoea agglomerans*-derived lipopolysaccharide (MACROPHI Inc.) (50 mg/mL) were prepared in doses for each administration group shown in Table 1. A phosphate buffer (NACALAI TESQUE, INC.) was added to the solutions to provide 100 µL of a vaccine composition. In Example 1, for example, 8.7 µL of the solution containing a *Streptococcus pneumoniae* capsule polysaccharide and 20 µL of the solution of a *Pantoea agglomerans*-derived lipopolysaccharide were mixed with each other, and then a phosphate buffer was added to the mixture to make the whole volume 100 µL. In the other examples and comparative examples, the solutions were appropriately diluted such that the amounts of the ingredients corresponded to the doses. In Comparative Example 4, neither vaccine antigen nor adjuvant was added and only a phosphate buffer (NACALAI TESQUE, INC.) was administered to mice.

Six mice (eight-week-old female BALB/C mice, Japan SLC, Inc.) were anesthetized, and then each mouse received 10 µL of the vaccine composition by nasal administration. One week after the administration, the mice were again anesthetized, and then each mouse received 10 µL of the vaccine composition by nasal administration. One week after the second administration, the serums and the nasal lavage fluids were collected from the respective mice. The Streptococcus pneumoniae-specific IgG titer in the serum and the *Streptococcus pneumoniae*-specific IgA titer in the nasal lavage fluid were measured by ELISA.

In the administration group with 1000 µg of the adjuvant (Comparative Example 1), the mice showed a bad coat of hair and weight loss 24 hours after the first administration, so that they were euthanized. Thus, the antibody titers were not measured. The adjuvant is a substance which activates the immunity and it clearly gives better immunity as the amount of the adjuvant increases. Still, administration of an excessive amount of the adjuvant causes safety issues, so that 1000-µg administration to the mice was never performed after Comparative Example 1.

The measuring method will be described in detail below.

TABLE 1

| No. | Vaccine antigen Species | Vaccine antigen Amount [µg/mouse/dose] | Adjuvant (LPS derived from Pantoea agglomerans) Amount [µg/mouse/dose] | Ratio (adjuvant/ antigen) | Administration route |
|---|---|---|---|---|---|
| Comparative Example 1 | Streptococcus pneumoniae capsule polysaccharide Pneumovax NP | 1 | 1000 | 1000 | Intranasal |

TABLE 1-continued

| No. | Vaccine antigen Species | Amount [μg/mouse/dose] | Adjuvant (LPS derived from Pantoea agglomerans) Amount [μg/mouse/dose] | Ratio (adjuvant/ antigen) | Administration route |
|---|---|---|---|---|---|
| Example 1 | Streptococcus pneumoniae capsule polysaccharide Pneumovax NP | 1 | 100 | 100 | Intranasal |
| Example 2 | Streptococcus pneumoniae capsule polysaccharide Pneumovax NP | 1 | 10 | 10 | Intranasal |
| Example 3 | Streptococcus pneumoniae capsule polysaccharide Pneumovax NP | 1 | 1 | 1 | Intranasal |
| Example 4 | Streptococcus pneumoniae capsule polysaccharide Pneumovax NP | 1 | 0.1 | 0.1 | Intranasal |
| Example 5 | Streptococcus pneumoniae capsule polysaccharide Pneumovax NP | 1 | 0.01 | 0.01 | Intranasal |
| Comparative Example 2 | Streptococcus pneumoniae capsule polysaccharide Pneumovax NP | 1 | 0.001 | 0.001 | Intranasal |
| Comparative Example 3 | Streptococcus pneumoniae capsule polysaccharide Pneumovax NP | 1 | 0 | 0 | Intranasal |
| Comparative Example 4 | — | — | — | — | Intranasal |

Examples 6 to 10, Comparative Examples 5 to 7

Vaccine compositions shown in Table 2 were prepared in manners similar to those in Examples 1 to 5 and Comparative Examples 1 to 4 except that a solution containing a HPV16 recombinant protein (HPV16, PROSPEC) (820 μg/mL) was used instead of the solution containing a *Streptococcus pneumoniae* capsule polysaccharide. In Example 6, for example, a solution containing a HPV16 recombinant protein (12.2 μL) and a solution of a *Pantoea agglomerans*-derived lipopolysaccharide (20 μL) were mixed with each other, and then a phosphate buffer was added to the mixture to make the whole volume 100 μL.

Six mice (eight-week-old female BALB/C mice, Japan SLC, Inc.) were anesthetized, and then each mouse received 10 μL of the vaccine composition by nasal administration. One week after the administration, the mice were again anesthetized, and then each mouse received 10 μL of the vaccine composition by nasal administration. One week after the second administration, the serum and the nasal lavage fluid were collected from the respective mice. The HPV16 recombinant protein-specific IgG titer in the serum and the HPV16 recombinant protein-specific IgA titer in the nasal lavage fluid were measured by ELISA. The measuring method will be described in detail below.

TABLE 2

| No. | Vaccine antigen Species | Amount [μg/mouse/dose] | Adjuvant (LPS derived from Pantoea agglomerans) Amount [μg/mouse/dose] | Ratio (adjuvant/ antigen) | Administration route |
|---|---|---|---|---|---|
| Example 6 | HPV16 recombinant protein | 1 | 100 | 100 | Intranasal |
| Example 7 | HPV16 recombinant protein | 1 | 10 | 10 | Intranasal |

TABLE 2-continued

| No. | Vaccine antigen Species | Amount [μg/mouse/dose] | Adjuvant (LPS derived from Pantoea agglomerans) Amount [μg/mouse/dose] | Ratio (adjuvant/ antigen) | Administration route |
|---|---|---|---|---|---|
| Example 8 | HPV16 recombinant protein | 1 | 1 | 1 | Intranasal |
| Example 9 | HPV16 recombinant protein | 1 | 0.1 | 0.1 | Intranasal |
| Example 10 | HPV16 recombinant protein | 1 | 0.01 | 0.01 | Intranasal |
| Comparative Example 5 | HPV16 recombinant protein | 1 | 0.001 | 0.001 | Intranasal |
| Comparative Example 6 | HPV16 recombinant protein | 1 | 0 | 0 | Intranasal |
| Comparative Example 7 | — | — | — | — | Intranasal |

Examples 11 to 13, Comparative Example 8

A solution containing live attenuated rotaviruses (ROTATEQ oral liquid, MSD K.K.) (50 μL) was mixed with a solution of a *Pantoea agglomerans*-derived lipopolysaccharide (2 mg/mL) (NACALAI TESQUE, INC.) (50 μL in Example 11; 5 μL in Example 12; or 0.5 μL in Example 13) or a solution of a glucopyranosyl lipid (2 mg/mL) (MPLAs, InvivoGen) (5 μL) in Comparative Example 8. A phosphate buffer (NACALAI TESQUE, INC.) was then added to the mixture to provide 100 μL of a vaccine composition. Six mice (eight-week-old female BALB/C mice, Japan SLC, Inc.) were anesthetized, and then each mouse received 10 μL of the vaccine composition by nasal administration. One week after the administration, the mice were again anesthetized, and then each mouse received 10 μL of the vaccine composition by nasal administration. One week after the second administration, the serum and the nasal lavage fluid were collected from the respective mice. The antigen-specific IgG titer in the serum and the antigen-specific IgA titer in the nasal lavage fluid were measured by ELISA.

Examples 14 to 52, Comparative Examples 9 to 21

Examples 14 to 16 and Comparative Example 9 used an inactivated poliovirus-containing solution (IMOVAX POLIO subcutaneous, Sanofi K.K.). Examples 17 to 19 and Comparative Example 10 used an inactivated hepatitis A virus-containing solution (Aimmugen, Kaketsuken (The Chemo-Sero-Therapeutic Research Institute)). Examples 20 to 22 and Comparative Example 11 used an inactivated Japanese encephalitis virus-containing solution (ENCEVAC for hypodermic injection, Kaketsuken (The Chemo-Sero-Therapeutic Research Institute)). Examples 23 to 25 and Comparative Example 12 used a live attenuated mumps virus-containing solution (live mumps vaccine, Kitasato Daiichi Sankyo Vaccine Co., Ltd.). Examples 26 to 28 and Comparative Example 13 used a live attenuated measles virus-containing solution (live measles vaccine, Kitasato Daiichi Sankyo Vaccine Co., Ltd.). Examples 29 to 31 and Comparative Example 14 used a live attenuated rubella virus-containing solution (dried live attenuated rubella vaccine, Kitasato Daiichi Sankyo Vaccine Co., Ltd.). Examples 32 to 34 and Comparative Example 15 used a tetanus toxoid-conjugated Haemophilus influenzae type b polysaccharide-containing solution (ActHIB, Sanofi K.K.). Examples 35 to 37 and Comparative Example 16 used a recombinant HBs antigen protein-containing solution (Bimmugen, Kaketsuken (The Chemo-Sero-Therapeutic Research Institute)). Examples 38 to 40 and Comparative Example 17 used a live attenuated yellow fever virus-containing solution (yellow fever vaccine, Sanofi K.K.). Examples 41 to 43 and Comparative Example 18 used a tetanus toxoid-containing solution (tetanus toxoid, DENKA SEIKEN CO., LTD.). Examples 44 to 46 and Comparative Example 19 used a live attenuated varicella-zoster virus-containing solution (dried live attenuated varicella vaccine, The Research Foundation for Microbial Diseases of Osaka University). Examples 47 to 49 and Comparative Example 20 used a live BCG-containing solution (dried BCG vaccine, Japan BCG Laboratory). Examples 50 to 52 and Comparative Example 21 used an inactivated rabies virus-containing solution (Inactivated Tissue Culture Rabies Vaccine, Kaketsuken (The Chemo-Sero-Therapeutic Research Institute)). The vaccine compositions as shown in Table 3 were prepared in a manner similar to that in Examples 11 to 13 and Comparative Example 8. The immunity tests were performed in a manner similar to that in Examples 11 to 13 and Comparative Example 8.

TABLE 3

| No. | Vaccine antigens Species | Amount [/mouse/dose] | Adjuvant Substance name | Ligand | Amount [mg/mouse/dose] | Administration route | Note |
|---|---|---|---|---|---|---|---|
| Example 11 | Live attenuated *rotavirus* (RIX4414 strain) | Vaccine 5 μL equivalent | LPS derived from *Pantoea agglomerans* | TLR4 | 10 | Intranasal | Liquid |
| Example 12 | Live attenuated *rotavirus* (RIX4414 strain) | Vaccine 5 μL equivalent | LPS derived from *Pantoea agglomerans* | TLR4 | 1 | Intranasal | Liquid |
| Example 13 | Live attenuated *rotavirus* (RIX4414 strain) | Vaccine 5 μL equivalent | LPS derived from *Pantoea agglomerans* | TLR4 | 0.1 | Intranasal | Liquid |
| Example 14 | Inactivated *poliovirus* (type 1, type 2, type 3) | Vaccine 5 μL equivalent | LPS derived from *Pantoea agglomerans* | TLR4 | 10 | Intranasal | Liquid |
| Example 15 | Inactivated *poliovirus* (type 1, type 2, type 3) | Vaccine 5 μL equivalent | LPS derived from *Pantoea agglomerans* | TLR4 | 1 | Intranasal | Liquid |
| Example 16 | Inactivated *poliovirus* (type 1, type 2, type 3) | Vaccine 5 μL equivalent | LPS derived from *Pantoea agglomerans* | TLR4 | 0.1 | Intranasal | Liquid |
| Example 17 | Inactivated hepatitis A virus | Vaccine 5 μL equivalent | LPS derived from *Pantoea agglomerans* | TLR4 | 10 | Intranasal | Liquid |
| Example 18 | Inactivated hepatitis A virus | Vaccine 5 μL equivalent | LPS derived from *Pantoea agglomerans* | TLR4 | 1 | Intranasal | Liquid |
| Example 19 | Inactivated hepatitis A virus | Vaccine 5 μL equivalent | LPS derived from *Pantoea agglomerans* | TLR4 | 0.1 | Intranasal | Liquid |
| Example 20 | Inactivated Japanese encephalitis virus | Vaccine 5 μL equivalent | LPS derived from *Pantoea agglomerans* | TLR4 | 10 | Intranasal | Liquid |
| Example 21 | Inactivated Japanese encephalitis virus | Vaccine 5 μL equivalent | LPS derived from *Pantoea agglomerans* | TLR4 | 1 | Intranasal | Liquid |
| Example 22 | Inactivated Japanese encephalitis virus | Vaccine 5 μL equivalent | LPS derived from *Pantoea agglomerans* | TLR4 | 0.1 | Intranasal | Liquid |
| Example 23 | Live attenuated *mumps virus* | Vaccine 5 μL equivalent | LPS derived from *Pantoea agglomerans* | TLR4 | 10 | Intranasal | Liquid |
| Example 24 | Live attenuated *mumps virus* | Vaccine 5 μL equivalent | LPS derived from *Pantoea agglomerans* | TLR4 | 1 | Intranasal | Liquid |
| Example 25 | Live attenuated *mumps virus* | Vaccine 5 μL equivalent | LPS derived from *Pantoea agglomerans* | TLR4 | 0.1 | Intranasal | Liquid |
| Example 26 | Live attenuated *measles virus* | Vaccine 5 μL equivalent | LPS derived from *Pantoea agglomerans* | TLR4 | 10 | Intranasal | Liquid |
| Example 27 | Live attenuated *measles virus* | Vaccine 5 μL equivalent | LPS derived from *Pantoea agglomerans* | TLR4 | 1 | Intranasal | Liquid |
| Example 28 | Live attenuated *measles virus* | Vaccine 5 μL equivalent | LPS derived from *Pantoea agglomerans* | TLR4 | 0.1 | Intranasal | Liquid |
| Example 29 | Live attenuated *rubella virus* | Vaccine 5 μL equivalent | LPS derived from *Pantoea agglomerans* | TLR4 | 10 | Intranasal | Liquid |
| Example 30 | Live attenuated *rubella virus* | Vaccine 5 μL equivalent | LPS derived from *Pantoea agglomerans* | TLR4 | 1 | Intranasal | Liquid |
| Example 31 | Live attenuated *rubella virus* | Vaccine 5 μL equivalent | LPS derived from *Pantoea agglomerans* | TLR4 | 0.1 | Intranasal | Liquid |
| Example 32 | Tetanus toxoid-conjugated *Haemophilus influenzae* type b polysaccharide | Vaccine 5 μL equivalent | LPS derived from *Pantoea agglomerans* | TLR4 | 10 | Intranasal | Liquid |
| Example 33 | Tetanus toxoid-conjugated *Haemophilus influenzae* type b polysaccharide | Vaccine 5 μL equivalent | LPS derived from *Pantoea agglomerans* | TLR4 | 1 | Intranasal | Liquid |
| Example 34 | Tetanus toxoid-conjugated *Haemophilus influenzae* type b polysaccharide | Vaccine 5 μL equivalent | LPS derived from *Pantoea agglomerans* | TLR4 | 0.1 | Intranasal | Liquid |
| Example 35 | Recombinant HBs antigen protein | Vaccine 5 μL equivalent | LPS derived from *Pantoea agglomerans* | TLR4 | 10 | Intranasal | Liquid |
| Example 36 | Recombinant HBs antigen protein | Vaccine 5 μL equivalent | LPS derived from *Pantoea agglomerans* | TLR4 | 1 | Intranasal | Liquid |
| Example 37 | Recombinant HBs antigen protein | Vaccine 5 μL equivalent | LPS derived from *Pantoea agglomerans* | TLR4 | 0.1 | Intranasal | Liquid |
| Example 38 | Live attenuated *yellow fever virus* | Vaccine 5 μL equivalent | LPS derived from *Pantoea agglomerans* | TLR4 | 10 | Intranasal | Liquid |
| Example 39 | Live attenuated *yellow fever virus* | Vaccine 5 μL equivalent | LPS derived from *Pantoea agglomerans* | TLR4 | 1 | Intranasal | Liquid |
| Example 40 | Live attenuated *yellow fever virus* | Vaccine 5 μL equivalent | LPS derived from *Pantoea agglomerans* | TLR4 | 0.1 | Intranasal | Liquid |
| Example 41 | Tetanus toxoid | Vaccine 5 μL equivalent | LPS derived from *Pantoea agglomerans* | TLR4 | 10 | Intranasal | Liquid |
| Example 42 | Tetanus toxoid | Vaccine 5 μL equivalent | LPS derived from *Pantoea agglomerans* | TLR4 | 1 | Intranasal | Liquid |
| Example 43 | Tetanus toxoid | Vaccine 5 μL equivalent | LPS derived from *Pantoea agglomerans* | TLR4 | 0.1 | Intranasal | Liquid |
| Example 44 | Live attenuated varicella-zoster virus | Vaccine 5 μL equivalent | LPS derived from *Pantoea agglomerans* | TLR4 | 10 | Intranasal | Liquid |
| Example 45 | Live attenuated varicella-zoster virus | Vaccine 5 μL equivalent | LPS derived from *Pantoea agglomerans* | TLR4 | 1 | Intranasal | Liquid |
| Example 46 | Live attenuated varicella-zoster virus | Vaccine 5 μL equivalent | LPS derived from *Pantoea agglomerans* | TLR4 | 0.1 | Intranasal | Liquid |
| Example 47 | Live BCG | Vaccine 5 μL equivalent | LPS derived from *Pantoea agglomerans* | TLR4 | 10 | Intranasal | Liquid |

TABLE 3-continued

| No. | Vaccine antigens Species | Amount [/mouse/dose] | Adjuvant Substance name | Ligand | Amount [mg/mouse/dose] | Administration route | Note |
|---|---|---|---|---|---|---|---|
| Example 48 | Live BCG | Vaccine 5 μL equivalent | LPS derived from Pantoea agglomerans | TLR4 | 1 | Intranasal | Liquid |
| Example 49 | Live BCG | Vaccine 5 μL equivalent | LPS derived from Pantoea agglomerans | TLR4 | 0.1 | Intranasal | Liquid |
| Example 50 | Inactivated rabies virus | Vaccine 5 μL equivalent | LPS derived from Pantoea agglomerans | TLR4 | 10 | Intranasal | Liquid |
| Example 51 | Inactivated rabies virus | Vaccine 5 μL equivalent | LPS derived from Pantoea agglomerans | TLR4 | 1 | Intranasal | Liquid |
| Example 52 | Inactivated rabies virus | Vaccine 5 μL equivalent | LPS derived from Pantoea agglomerans | TLR4 | 0.1 | Intranasal | Liquid |
| Comparative Example 8 | Live attenuated rotavirus (RIX4414 strain) | Vaccine 5 μL equivalent | Glucopyranosyl lipid | TLR4 | 1 | Intranasal | Liquid |
| Comparative Example 9 | Inactivated poliovirus (type 1, type 2, type 3) | Vaccine 5 μL equivalent | Glucopyranosyl lipid | TLR4 | 1 | Intranasal | Liquid |
| Comparative Example 10 | Inactivated hepatitis A virus | Vaccine 5 μL equivalent | Glucopyranosyl lipid | TLR4 | 1 | Intranasal | Liquid |
| Comparative Example 11 | Inactivated Japanese encephalitis virus | Vaccine 5 μL equivalent | Glucopyranosyl lipid | TLR4 | 1 | Intranasal | Liquid |
| Comparative Example 12 | Live attenuated mumps virus | Vaccine 5 μL equivalent | Glucopyranosyl lipid | TLR4 | 1 | Intranasal | Liquid |
| Comparative Example 13 | Live attenuated measles virus | Vaccine 5 μL equivalent | Glucopyrancsyl lipid | TLR4 | 1 | Intranasal | Liquid |
| Comparative Example 14 | Live attenuated rubella virus | Vaccine 5 μL equivalent | Glucopyranosyl lipid | TLR4 | 1 | Intranasal | Liquid |
| Comparative Example 15 | Tetanus toxoid-conjugated Haemophilus influenzae type b polysaccharide | Vaccine 5 μL equivalent | Glucopyranosyl lipid | TLR4 | 1 | Intranasal | Liquid |
| Comparative Example 16 | Recombinant HBs antigen protein | Vaccine 5 μL equivalent | Glucopyranosyl lipid | TLR4 | 1 | Intranasal | Liquid |
| Comparative Example 17 | Live attenuated yellow fever virus | Vaccine 5 μL equivalent | Glucopyranosyl lipid | TLR4 | 1 | Intranasal | Liquid |
| Comparative Example 18 | Tetanus toxoid | Vaccine 5 μL equivalent | Glucopyranosyl lipid | TLR4 | 1 | Intranasal | Liquid |
| Comparative Example 19 | Live attenuated varicella-zoster virus | Vaccine 5 μL equivalent | Glucopyranosyl lipid | TLR4 | 1 | Intranasal | Liquid |
| Comparative Example 20 | Live BCG | Vaccine 5 μL equivalent | Glucopyranosyl lipid | TLR4 | 1 | Intranasal | Liquid |
| Comparative Example 21 | Inactivated rabies virus | Vaccine 5 μL equivalent | Glucopyranosyl lipid | TLR4 | 1 | Intranasal | Liquid |

(Mouse Immunity Test)

The vaccine composition was administered to an eight-week-old female BALB/c mouse twice at a one-week interval. One week after the final administration, the blood and the nasal lavage fluid was collected from the mouse. The blood was centrifuged at 3000 G at 4° C. for 10 minutes. The serum (20 ρL) was mixed with a phosphate buffer (NACALAI TESQUE, INC.) (300 μL) to provide a serum sample. The nasal lavage fluid was collected as follows. Specifically, a slit was formed at the lower portion of the respiratory tract of the BALB/c mouse, and 200 μL of a phosphate buffer (NACALAI TESQUE, INC.) was poured into the respiratory tract through the slit to allow the buffer to flown out of the nasal cavity. This flown-out sample was collected as a nasal lavage fluid sample.

The Streptococcus pneumoniae- or HPV16 recombinant protein-specific IgG titer in the mouse serum was measured, thereby evaluating the systemic immune response. The Streptococcus pneumoniae- or HPV16 recombinant protein-specific IgA titer in the nasal lavage fluid of mouse was measured, thereby evaluating the mucosal immune response. The methods of evaluating the titers will be described below.

Figure 1:
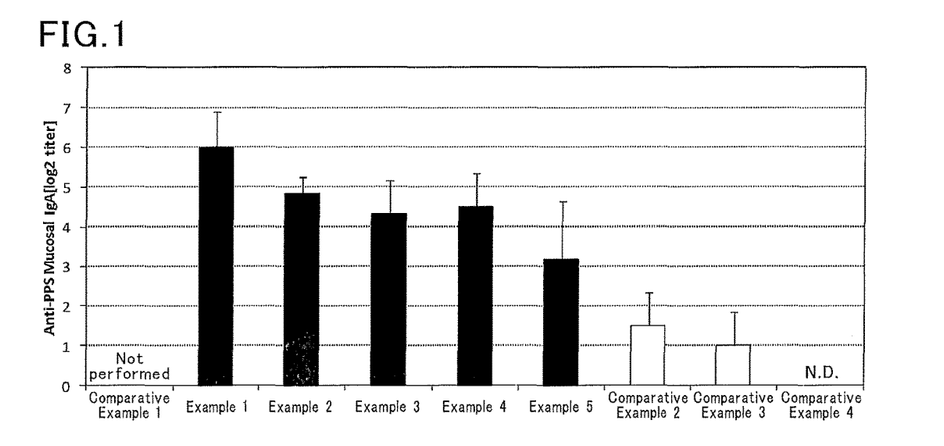
FIG. 1 is a graph showing the results of measuring the *Streptococcus pneumoniae*-specific IgA titers in mouse nasal lavage fluid in Examples 1 to 5 and Comparative Examples 1 to 4.
Figure 2:
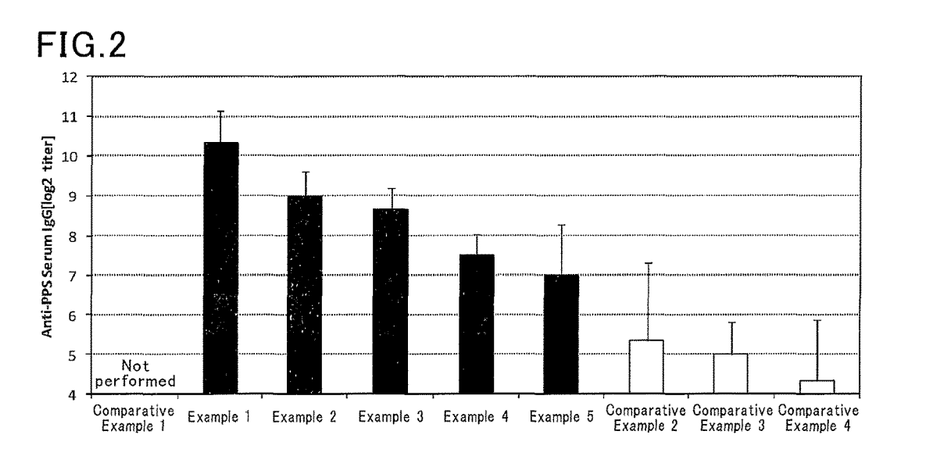
FIG. 2 is a graph showing the results of measuring the *Streptococcus pneumoniae*-specific IgG titers in mouse serum in Examples 1 to 5 and Comparative Examples 1 to 4.
Figure 3:
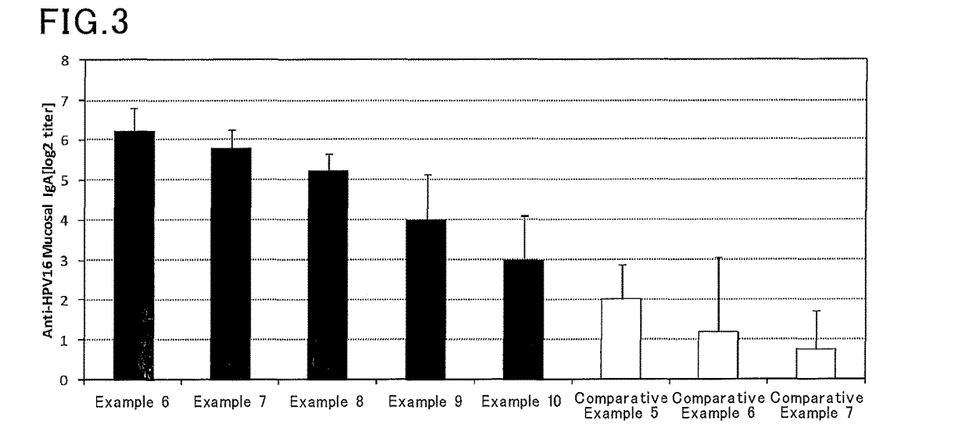
FIG. 3 is a graph showing the results of measuring the HPV16 recombinant protein-specific IgA titers in mouse nasal lavage fluid in Examples 6 to 10 and Comparative Examples 5 to 7.
Figure 4:
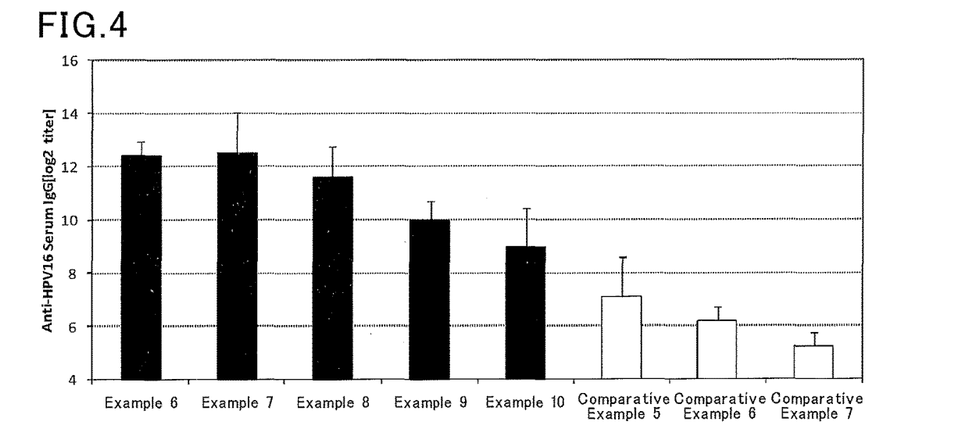
FIG. 4 is a graph showing the results of measuring the HPV16 recombinant protein-specific IgG titers in mouse serum in Examples 6 to 10 and Comparative Examples 5 to 7.

FIGS. 1 to 4 show the respective evaluation results.

(Method of Measuring Antigen-specific IgG Titer in Mouse Serum (ELISA))

Each antigen was diluted with a carbonate buffer (for example, a solution of a Streptococcus pneumoniae capsule polysaccharide antigen was prepared for the measurement of a Streptococcus pneumoniae capsule polysaccharide-specific IgG antibody titer), and 100 μL portions of the diluted antigen (2.5 μg/mL) were put into the wells of a 96-well plate for ELISA. They were left to stand overnight.

The wells were then washed three times with a polysorbate (TWEEN 20)-containing PBS (hereinafter, referred to as a washing liquid) prepared in advance. A blocking agent (BLOCK ACE, DS Pharma Biomedical Co., Ltd.) was diluted to 4 g/400 mL with purified water to provide a blocking solution. Then, 200 μL portions of the blocking solution were added to the respective wells and left to stand for two hours at room temperature. Thereafter, the wells were washed three times with the washing liquid.

A blocking agent (BLOCK ACE, DS Pharma Biomedical Co., Ltd.) was diluted to 0.4 g/100 mL with a phosphate buffer (NACALAI TESQUE, INC.) to provide a solution (hereinafter, referred to as a diluted reagent). The aforementioned serum sample was serially diluted 2-fold 15 times using the diluted reagent. Then, 50 μL portions of the resulting solution were added to the wells, and left to stand for two hours at room temperature.

Next, the wells were washed three times using the washing liquid, and 100 μL portions of a TMB solution (ELISA POD TMB kit, NACALAI TESQUE, INC.) were added to the wells. Then, 100 μL portions of a 1 M sulfuric acid solution were added thereto, and the absorbance at 450 nm of the 96-well plate was measured using a microplate reader (168-11135CAM, Bio-Rad Laboratories, Inc.). Based on the absorbance values in the serial dilutions, the maximum dilution factor among the dilution factors with an absorbance of not breaking 0.1 was defined as the IgG titer in a mouse serum. The values were represented in terms of Log2.
(Method of Measuring Antigen-Specific IgA Titer in Nasal Lavage Fluid of Mouse (ELISA))

This method is fundamentally similar to the method of measuring an antigen-specific IgG titer. The measurement sample is a nasal lavage fluid, and a HRP-labeled anti-mouse IgA antibody (Goat-anti-mouse IgA a HRP, Bethyl Laboratories, Inc.) was used instead of the HRP-labeled anti-mouse IgG antibody. The other operations were performed in a similar manner.

FIGS. 1 to 4 show that the *Streptococcus pneumoniae*-or HPV16 recombinant protein-specific IgG and IgA were produced at high levels in the examples. In contrast, the *Streptococcus pneumoniae*- or HPV16recombinant protein-specific IgG and IgA were produced at low levels in the comparative examples.

These results prove that combination use of an antigen and a specific gram-negative bacterium-derived lipopolysaccharide or a salt thereof as an adjuvant is effective in inducing mucosal immunity at the nasal mucosa.

INDUSTRIAL APPLICABILITY

Since the nasal mucosal vaccine composition of the present invention contains at least one antigen together with the aforementioned specific adjuvant, it can safely and effectively induce systemic immune responses and mucosal immune responses.

The invention claimed is:

1. A method comprising:
   administering a nasal mucosal vaccine composition to a human or animal nasal mucous membrane, the nasal mucosal vaccine composition comprising:
   at least one antigen derived from a pathogen excluding antigens derived from influenza viruses; and
   as an adjuvant, a lipopolysaccharide derived from at least one gram-negative bacterium selected from the group consisting of *Pantoea, Acetobacter, Zymomonas,* and *Xanthomonas*, or a salt of the lipopolysaccharide.

2. The method according to claim 1, wherein a mass ratio between a total mass of the adjuvant and a total mass of the antigen is 0.002 to 500.

3. The method according to claim 1, wherein the method induces humoral immunity.

4. The method according to claim 2, wherein the method induces humoral immunity.

5. The method according to claim 1, wherein the lipopolysaccharide is derived from *Pantoea agglomerans*.

6. The method according to claim 1, wherein the mucosal vaccine composition is a spray, semi-solid medicine, or solid preparation.

* * * * *